United States Patent
Carlson (10) Patent No.: US 6,367,510 B1
(45) Date of Patent: Apr. 9, 2002

(54) TUBING PRODUCT HAVING A HELICAL SUPPORT BEAD WITH LUMEN AND METHOD

(76) Inventor: Eric Carlson, 12 Pegasus Dr., Coto De Caza, CA (US) 92679

( * ) Notice: Subject to any disclaimer, the term of this patent is extended or adjusted under 35 U.S.C. 154(b) by 0 days.

(21) Appl. No.: 09/585,976

(22) Filed: Jun. 2, 2000

(51) Int. Cl.[7] ................................................ F16L 11/08
(52) U.S. Cl. ...................... 138/121; 138/122; 138/129; 138/150
(58) Field of Search .................................. 138/129, 122, 138/154, 144, 172, 133, 173, 174, 121, 150

(56) References Cited

U.S. PATENT DOCUMENTS

| | | | | |
|---|---|---|---|---|
| 3,737,997 A | * | 6/1973 | Davis | 29/624 |
| 4,204,562 A | * | 5/1980 | Kelly | 138/129 X |
| 4,490,575 A | * | 12/1984 | Kutnyak | 138/129 X |
| 4,628,966 A | * | 12/1986 | Kanao | 138/129 X |
| 5,046,531 A | * | 9/1991 | Kanao | 138/122 |
| 5,975,144 A | * | 11/1999 | Akedo et al. | 138/129 |
| 6,158,477 A | * | 12/2000 | Waters | 138/129 |

* cited by examiner

Primary Examiner—Patrick Brinson
(74) Attorney, Agent, or Firm—Terry L. Miller (57) ABSTRACT

A helically wound and helically ribbed plastic tubing incorporating one or plural support beads with at least one of the support beads defining one or plural helical lumens. The support bead is free of joints or bonding lines extending between the lumen(s) and ambient so that the lumen is free of unintended fluid communication between the lumen and ambient, and the lumen is capable of transporting or containing gaseous or fluid materials without leakage. The support bead may encapsulate an electrical conductor, which may be a heating wire for the purpose of providing a heat source to fluid flow in the central passage of the tubing product. Alternatively, the electrical conductor may be an energy or signal conducting element suited for sensing purposes or data transmission along a length of the tubing, for example. A lumen termination fitting may connect to the tubing. Apparatus and methods for making the tubing product are also disclosed.

11 Claims, 9 Drawing Sheets

TUBING PRODUCT HAVING A HELICAL SUPPORT BEAD WITH LUMEN AND METHOD

BACKGROUND OF THE INVENTION

1. Field of the Invention

The present invention relates in general to plastic tubing and, more particularly, to apparatus and methods for making such tubing which is flexible and includes an external helical rib or bead.

2. Related Technology

Tubing which is flexible, and has a relatively thin wall and an integral helical supporting bead is known in the art. Such a flexible support-bead tubing construction provides substantial crush resistance while leaving the tube wall flexible enough to permit short-radius bends without collapsing or kinking the tube. The versatility of this kind of tubing is evidenced by its wide applicability in construction, ventilation, manufacturing processes, auto washes, medical devices, hospitals and other fields.

The walls of a support-bead tubing can be quite thin to minimize overall weight. This light weight for the tubing is an important feature when, for example, the tubing is used with an inhalation machine to provide a patient with more comfort during oxygen or medicated air delivery. Two other features of known thin wall support-bead or bead-reinforced tubing are transparency and smoothness of bore. Transparent plastic material permits inspection of the fluid coursing through the tube, to detect, for example, the presence of moisture in an anesthetic or patient oxygen delivery application. A smooth inner surface of such a tube is desirable to keep the tube free from deposits of contaminants and to discourage non-laminar flow. Also, this smooth inner surface makes the tubing product more desirable for applications in which the tubing is to be re-used. The smooth inner surface promotes easy and effective cleaning, sanitizing, and sterilizing of the tubing product.

U.S. Pat. No. 3,910,808 to Steward, discloses apparatus for forming a thin-walled, flexible, crush resistant tubing having a support-bead. Steward discloses a method for extruding a plastic strip having a longitudinal rib, and the method and apparatus for helically winding the strip about an axis to produce a corrugated flexible tubing having a smooth bore and a helical external support bead.

Many applications, however, require or are enhanced by the presence of controlled heating of such tubing. Neonatal patients, for example, as well as patients in shock or who are sustained on breathing equipment, are among those who benefit from gas flowing through heat-conditioned tubing.

U.S. Pat. No. 5,454,061 to Lenart Carlson, provides a helically wound and helically ribbed plastic tubing incorporating an electrically conductive heating wire and an apparatus and method for making the tubing. In this patent a plastic ribbon is wound about an axis into a tube with one edge of each lap overlapping and heat bonded to an edge of the preceding lap as the tubing is rotationally formed. A conductive wire is embedded in the ribbon and a bead is applied and heat-bonded onto the tubing, encapsulating the conductive wire during rotation of the tubing, and providing a unitary structure including a conductive wire integral to a flexible tubing. Again, the tubing has a corrugated crevice-free outside surface and a smooth inside surface. Coolant is applied to the tubing for cooling the unitary ribbon, wire, and bead during formation of the tubing, and also to assist in advancing the tubing along the axis of the manufacturing apparatus.

One prior application of a hollow ribbed pipe can be found in U.S. Pat. No. 5,051,081 assigned to Toyox. In this patent hollow ribs are produced by extrusion, and are then wrapped around the outer periphery of an extruded pipe. This construction of a tubing product has several deficiencies. For example, the interior walls of the hollow rib produced by this apparatus contain connection lines through which a gaseous material could escape into the ambient, and the rib is extruded in such fashion that it would not be possible to separate it from the tube and attach it to a hose barb. That is, the shape of the lumen or passage in this rib is not generally round.

SUMMARY OF THE INVENTION

A new application for such flexible tubing requires that a second lumen or passage be available for communication between the ends of the tubing. A preferred way of providing this second lumen or passage is to provide a lumen or passage inside and integrally defined by the support bead.

No prior product, method of manufacture, or apparatus is known which provides a transparent, sterilizable, thin-walled, smooth bore tube having a contemporaneously wound supporting and encapsulating bead defining a lumen, or defining plural lumens, each suitable for communicating a fluid between the ends of the tubing product, and with the bead, and tube forming a unitary structure with a smooth, crevice-free outer surface.

In view of the deficiencies of the related art as discussed above, it is a primary object of the present invention to provide a flexible, lightweight, crush-resistant tubing having one or plural supporting bead helically wound about and integral with the surface of the tubing. The is constructed with smooth walls free from joints or connection lines. The bead defines one lumen or plural lumens capable of transporting or communicating a fluid or gas without leakage to the ambient.

It is another object of this invention to provide apparatus and method for inexpensively making a tubing product, supporting bead with at least one interior lumen, and tube wall as a unitary body free of adhesive and binders and having a smoothly corrugated outer surface free of crevices.

Yet another object for this invention is to provide a method and apparatus for terminating the tubing product, providing for each of the central passage of the tubing and the lumen of the support bead to be connected to respective fittings in fluid flow relation.

These and other objects are achieved by the present invention which provides apparatus for combining a thin film or ribbon, and a supporting bead defining one lumen or plural lumens to make a flexible tubing, and provides a method for producing the tubing in a single winding and bonding operation. The present invention employs a winding mechanism which accepts in sequence: an extruded plastic flat ribbon, and one or plural extruded supporting bead(s). The ribbon is helically wrapped so that its edges overlap and simultaneously heat-bond to themselves to form a lap joint. A bead is laid atop the ribbon and heat-bonded to the ribbon at the lap joint, forming a unitary body as described below. If plural beads are used each in turn is wound around the tube parallel with the first in similar fashion. One or more of the beads defines a single or plural lumens extending helically along the tubing product. Each lumen inside the bead will retain the same approximate size and shape free from obstruction for the entire length of the tubing product. As the bead is extruded a small amount of regulated air or gas pressure is introduced into the lumen in such a fashion as to keep the lumen open, and to insure that it retains a uniform cross sectional size and shape.

Another embodiment of the invention utilizes the tubing body construction and support bead type as described above with the added feature of having a pair of electrical conductors encapsulated within the tubing body and immediately under the support bead. One use for such electrical conductors is as an electrical resistance heating conductor to offset heat loss to ambient from warmed tidal air flow in the tube. Another use for such an electrical conductor pair would be as an electrical link between an electrical sensor and a device responsive to this sensor.

While other heat-bondable plastics may be successfully used to make the flat ribbon which becomes the wall of the present tubing product, for a variety of medical applications a polyolefin plastomer such as EXACT™ is preferable. The properties of this material include chemical purity, reusability, transparency and resistance to damage from sterilization. Thermoplastic rubbers such as SANTOPRENE™, or thermoplastic elastomer such as SARLINK™, are suitable materials for ribbon formation, although their transparency is inferior to that of EXACT™. The bead material is chosen for its ability to heat-bond with the flat ribbon, and may be of the same composition as the ribbon or of a suitable compatible different composition including the materials just mentioned.

The method utilized in creating all embodiments of the invention are similar and each can be deduced from the following description. In this particular embodiment of the invention an electrical resistance heating conductor; which we shall heretofore refer to as wire is utilized. For heating purposes, the wire conductor is preferably a resistive metal such as nickel chromium alloy (i.e., nichrome wire).

The walls of the tubing are formed by overlapping, heat-bonding and cooling successive laps or convolutions of the flat ribbon as the ribbon is extruded onto canted and rotationally driven winding rolls. As in the Carlson '061 patent, the wire is aligned precisely along an edge of a ribbon convolution which is sufficiently cooled to prevent the wire from cutting completely through the thin ribbon, yet still warm enough to partially embed the wire in the ribbon.

The configuration of the support bead is defined by splayed or relatively angulated surfaces on either side of and cooperatively defining a wire-receiving recess. The surfaces are spread angularly apart in order to form a smooth, crevice-free juncture as the bead heat-bonds to the film while the recess receives the wire, the bead thereby surrounding the wire and integrating the ribbon, wire and bead into a unitary structure. In operation, the ribbon which will form the wall of the tubing product is extruded and helically wound onto the winding rolls, preferably from an elevated position with respect to the rolls so that any sag caused by relatively low viscosity of the extrudate is reduced or eliminated.

After several wraps of the ribbon are wound on the rolls, an electrical conductor, which may be a resistance wire, is paid out through a wire-feeding mechanism to a draw point adjacent to a lap joint of the rotating work piece. At the point the wire is applied, the work piece surface is still warm enough to partially embed the wire. Thereafter, the supporting bead is extruded over the wire on a lap joint selected so that the bead fully encapsulates the wire that is still partially embedded in the outer wall of the rotating tubing. This construction process is accomplished in such fashion as to provide not only a uniform outer shape and size for the bead, but also an interior bore of passage of uniform shape and size, and at least one lumen or passage in the bead as well.

The unitary construction just described has a significant advantage in addition to an inherent resistance to the accumulation of soil and bacteria on its outer surface, and an inherent supportive strength (i.e., from the helical bead). Since a primary purpose of the lumen defined by and within the support bead is for transference and containment of a gaseous or fluid material, it is important that this helical lumen be both capable of containment of such material (i.e., by being essentially leak-free) and likewise be capable of allowing the material to flow unhindered through the lumen of the bead from one end of a length of the tubing product to the other. Such a unitary tubing construction also allows substantial benefit to be derived by insulating the heating wire from ambient conditions, as is additionally accomplished by the encapsulating bead.

Further applications of the present invention will be apparent to those skilled in the art from consideration of several fully detailed exemplary embodiments described and depicted herein. To aid in the explanation of the exemplary embodiments, reference will be made to the Figures of the appended sheets of drawings, which Figures will first be described briefly. That is, the advantages and features of the present invention will be better understood in view of the following description of several exemplary preferred embodiments of the invention when considered in conjunction with the accompanying drawings in which:

DETAILED DESCRIPTION OF EXEMPLARY PREFERRED EMBODIMENTS OF THE INVENTION

Figure 1:
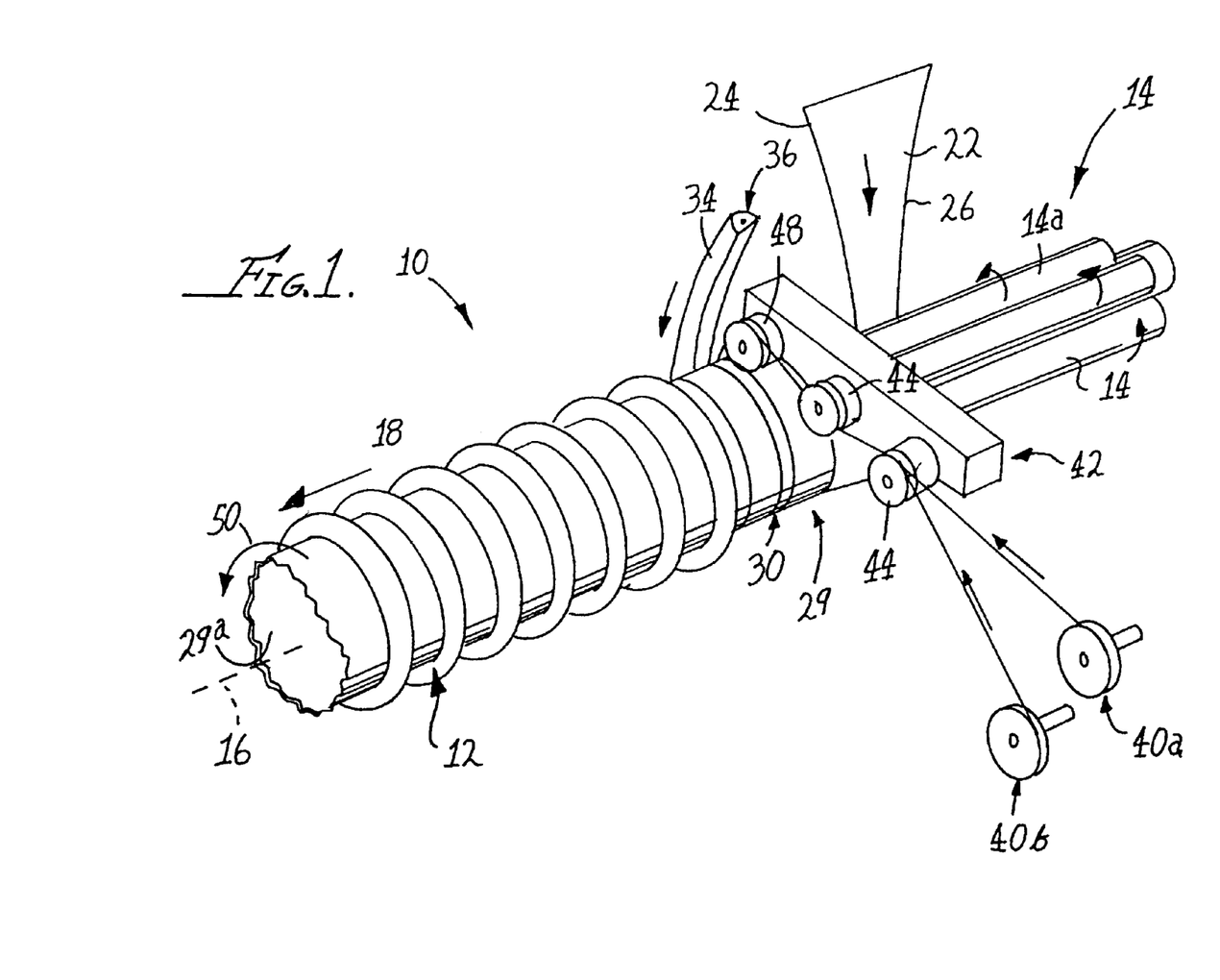
FIG. 1 is a schematic view showing the manufacturing apparatus and tubing product made using this apparatus according to features of an exemplary embodiment of the invention.
Figure 5:
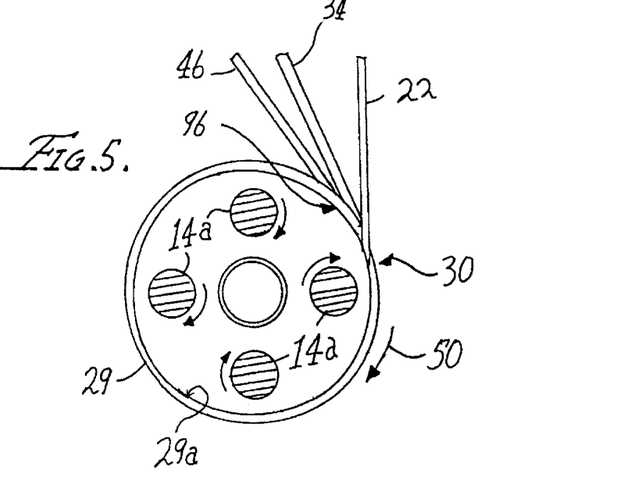
FIG. 5 is a section view taken along lines 5—5 of FIG. 1 with typical draw angles of extrudates and electrical conductor wire being shown for clarity, it is to be noted that the axial direction of view in FIG. 5 is opposite to that of FIGS. 2 and 3.

A manufacturing apparatus 10, which embodies a novel method of making a flexible multi-lumen tubing product 12 embodying the present invention, and the tubing product itself are both illustrated in the appended drawing Figures. FIG. 1 illustrates the manufacturing apparatus 10 including a compound winding mandrel 14 having four cantilevered and rotationally driven winding rolls 14a. Each of the winding rolls 14a is canted and is circumferentially spaced about a longitudinal axis 16 for winding and rotationally advancing the helically wound and ribbed heatable flexible tubing 12. Advancement of the tubing product 12 is shown by the directional arrow 18 in FIG. 1. The rolls 14a rotate in unison in a clockwise direction when viewed in the direction of tubing movement along axis 16, as is illustrated in FIG. 5.

Figure 2:
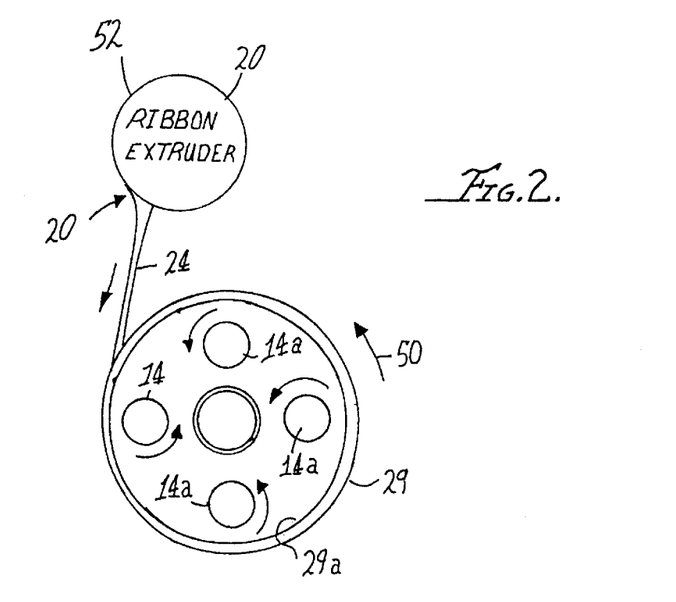
FIGS. 2 and 3 are fragmentary axial views, partly in cross section, showing steps in the method of making a tubing product according to the invention.

The manufacturing apparatus 10 includes also a first extruder 20, best seen in FIG. 2, for extruding a heat bondable flat ribbon 22 of molten polymer extrudate having a leading edge 24 and trailing edge 26. Ribbon 22 is wrapped about the rolls 14a and is advanced helically toward the left, viewing FIG. 1, so that it encircles the rolls 14a and wraps helically upon itself with a certain overlap to form successive convolutions or wraps 28 of a tubular body 29 having an internal passage 29a. The adjacent convolutions or wraps of the ribbon 22 are heat-bonded to adjacent convolutions forming a lap joint 30 cooperatively defined by overlapping marginal edge portions of each wrap of the ribbon 22 defining the tubular body 29.

Figure 3:
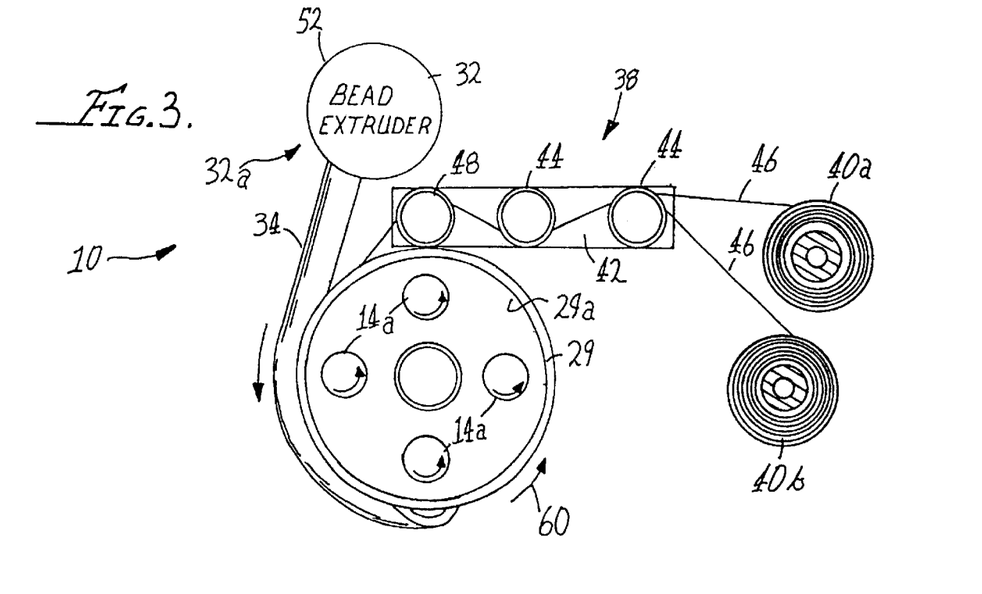
Figure 4:
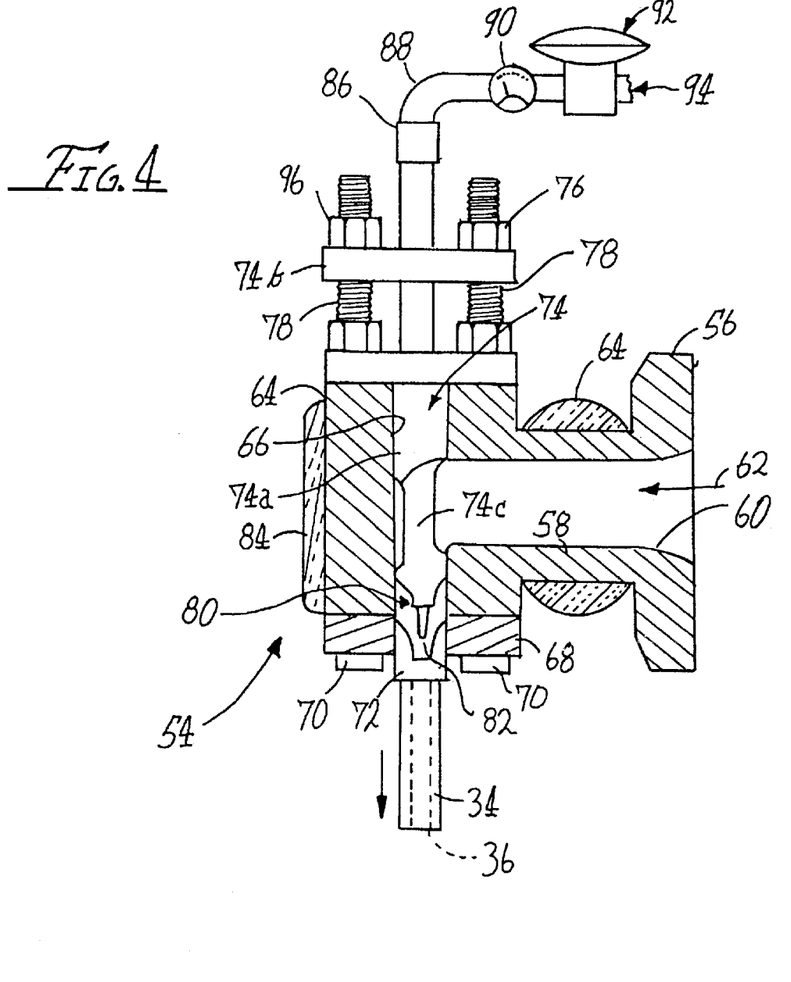
FIG. 4 is view of the crosshead utilized in extruding a molten polymer extrudate defining a lumen, which then becomes a helical support bead with a helical lumen of the tubing product according to this invention.

The apparatus 10 also includes a second extruder 32 best seen in FIGS. 3 and 4, for extruding a heat bondable support bead 34 containing a passage or lumen 36. Although the extruders 20 and 32 are shown as physically separate components for ease of explanation in FIG. 1, it should be understood that both ribbon 22 and bead 34 may be extruded from a single extruder, perhaps by use of co-located dies on a single extruder head, and corresponding to very small draw angles between the ribbon and bead extrudates, as described later with reference to FIG. 5.

Referring again to FIG. 1, apparatus 10 includes a wire feeding or payout mechanism 38 (also seen in FIG. 3), which is exemplary and may include, for example, one or a pair of 35 spools 40a, 40b, each with a tension control mechanism 42 having a number of wire straightening and guiding rolls 44. The spools 40a, 40b each holds and pays out a supply of electrically conductive wire 46, which is positioned and embedded in the tubing product along the leading edge 24 of each convolution or lap of the ribbon 22 just prior to application of the support bead 34 to the tube 12 as shown. This placement of the conductive wires 46 is accomplished through the use of guide rollers 48 to provide the proper alignment and tension on the wires 46 as the tubular body 12 rotates, as is signified by the directional arrow 50.

The process of extruding both the ribbon 22 and the support bead 34 creates considerable heat; which must be removed from the tubular body 12. This is accomplished by injecting water onto the tubular body 12 after the support bead 34 has bonded with the ribbon 22. To further explain the manufacturing process, it is seen that in order to provide the multiple molten plastic elements which are combined on mandrel 14 to form the tubing product 12, a pair of melt extruders 20, 32 are employed. The respective extruder heads are best seen in FIGS. 2 and 3, which provide diagrammatic views looking axially opposite to the direction of advancement of tubing product 12. These extruders 20 and 32 have extruder heads 20a and 32a which typically have strap-on electrical heater jackets 52 to controllably maintain the extruder heads at a selectively elevated temperature.

The ribbon 22 is issued from the extruder head 22a and elongates partly due to its own weight and rather low viscosity, and partly due to its being pulled toward the mandrel 14 by the rotation of the rolls 14a, such that this ribbon is wrapped upon itself in an overlapping fashion such as to form the wall of the tubular body 29 as is seen in FIG. 1. This is accomplished by feeding the ribbon 22 onto the canted or angulated winding rolls 14a so that the angulation and rotation of these rolls causes the ribbon 22 to advance axially and helically forward (i.e., arrow 18) in a controlled manner so that it encircles the rollers and wraps upon itself with a certain overlap to form the helical lap joint 30 as is seen in cross sectional view in FIG. 8.

After at least two convolutions of ribbon 22 have been wrapped on the rolls 14a, then one or more of the wires 46 are circumferentially fed onto the outer surface of the thin-walled tubular body 29 of the tubing product 12. Since the ribbon 22 is still partially molten at this time the wires 46 are partially embedded into the surface of the ribbon 22 adjacent to the lap joint 30. Because the ribbon is partially cooled, and because the wire 46 is laid on with a light and controlled tension, the wire 46 does not cut through the ribbon 22.

This wire 46 is then covered over by the support bead 34, as can be seen in FIG. 1 and 3. The bead 34 is extruded from the bead extruder head assembly 54 seen in FIGS. 3 and 4. Looking particularly at FIG. 4, the construction of the bead extruder crosshead assembly 54 can be seen in cross section. This crosshead assembly 54 includes a flange portion 56, which is secured by a band clamp (not shown) to a similar flange (not shown) disposed at the outlet end of the barrel (not shown) of the second extruder 32. This flange 56 carries a neck portion 58. The flange 56 and neck 58 cooperatively define a central passage 60 into which is received the pressurized molten polymer issuing from extruder 32, as is indicated by arrow 62. This polymer flows from the neck portion 58 to a cross head body 64 carried by this neck portion, and to a through bore 66 defined in this cross head body.

The crosshead body portion 64 has a die holder 68 attached to it with fasteners 70. This die holder 68 holds a die 72 in place during extrusion of the bead 34. The die defines an opening which defines the outer shape of the extrudate issuing from this die, and becoming the bead 34 of the tubing product 12 (see, FIG. 6). The opposite end of the crosshead body 64 supports a tip holder 74, which includes a hollow shaft portion 74a and a flange part 74b. The flange part 74b is positioned by a pair of nuts 76 carried on studs 78. The nuts 76 allow for axial adjustment of the tip holder shaft portion 74a relative to the cross head body 64. The shaft portion 74a defines recesses 74c leading the molten polymer flow 62 toward the forward portion of the shaft 74a, at which this shaft defines a tip holder feature, indicated by arrowed numeral 80. An outwardly conical and tubular tip 82 is carried on the shaft 74a, and is axially movable relative to the die 72 by adjustments of the nuts 76. The neck portion 58 and cross head body 64 each carry heater bands 84, so that the cross head assembly 54 can be maintained at a selected elevated temperature.

As is seen in FIG. 4, the tip holder 74 has an air connection at 86, to which is connected a conduit 88 leading from a pressure gauge 90, and a regulator valve 92. The regulator valve 92 receives pressurized air, as is indicated by arrow 94. The air is valved to a regulated pressure, and is delivered via the tip holder 74 and tip 82. Thus, it is to be understood that as molten polymer is fed into the crosshead through the passage 60 (arrow 62) it passes through the neck portion 58 and along the bore 66 and recesses 74c to issue from the die 72. As the bead 34 is formed in the die 72 the lumen 36 is created in this bead by the tip 82. As the bead 34 leaves the die 72, and is elongated toward and to its wrapping upon the tubular body 29, the lumen 36 is kept open by a small volume of pressurized air injected through the tip 82, as is selectably controlled by the regulator valve 92. This regulated air pressure in the lumen may be read on the pressure gauge 92 so that an accurate and repeatable pressure in the lumen may be set and maintained.

Figure 6:
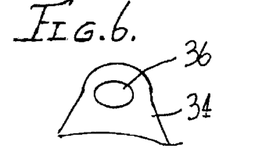
FIG. 6 is a fragmentary cross section view of a bead portion of the flexible tubing product and is shown at an enlarged size.
Figure 9:
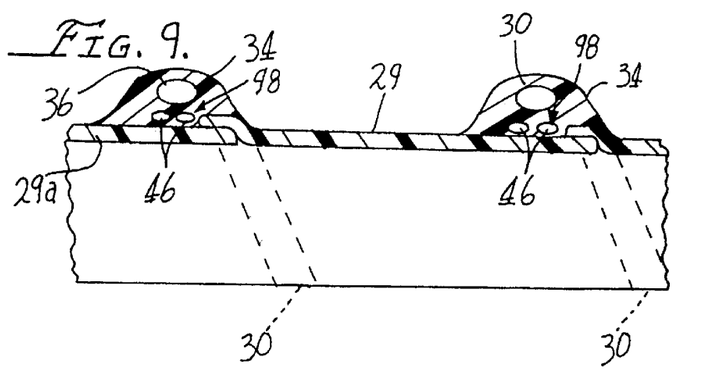
FIG. 9 provides an enlarged fragmentary cross-sectional view of one embodiment of a tubing product according to the present invention.
Figure 11:
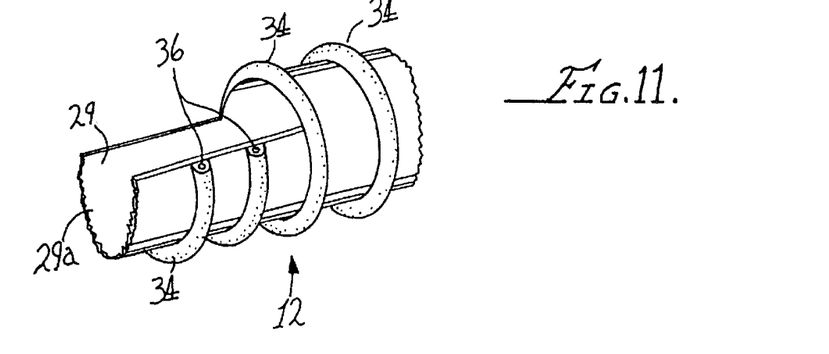
FIG. 11 is a partially cut away perspective view of a tubing product according to this invention, and in an substantially straight or unflexed condition.

FIG. 1 illustrates the manufacturing process with the ribbon 22 descending onto the rolls 14a from the right of support the bead 34 (as viewed axially in the direction of arrow 18). However, it should be noted that the ribbon 22 and support bead 34 may travel onto the rolls 14a from positions interchanged from that shown in FIG. 1. As is illustrated in FIG. 5 the support bead 34 is fed onto each lap 30 at a point following a draw point 96 of the wire 46. The draw point 96 is the tangential point at which the wire 46 lays upon the ribbon 22, and from which this wire 46 then wraps about the tubular body 29. As can be seen in FIGS. 6, 9, and 11 this process is accomplished while maintaining a stable uniform shape and size for both the exterior of the support bead 34 and the smooth-walled lumen 36 inside this support bead. This is accomplished as was explained above, by applying regulated air flow 94 into the lumen 36 while the support bead 34 is being extruded, extends to the tubular body 29, and is applied over the lap joint 30 of the helically wrapped and bonded ribbon 22. The bead completely encapsulates the wire(s) 46.

Figure 7:
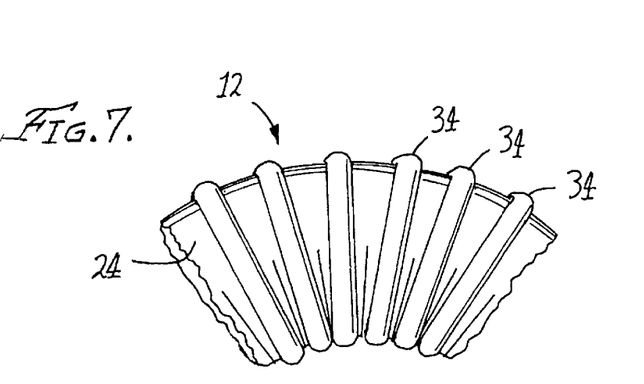
FIG. 7 is an elevated view of the tubing product in a flexed condition.

Further, the lumen 36 is maintained open entirely along its helical length from one end of a length of the tubing product 12 to the other end of such a length. Thus, the lumen 36 may be used to conduct, for example, a pressurized fluid along the length of the tubing product 12, in addition to whatever fluid may flow in the passage 29a of the tubing itself. FIG. 11 also depicts a sectioned view of a length of the tubing product 12 in which the lumen 36 can be seen. This tubing product 12 is also seen in FIG. 7, but is shown in a flexed position. As is seen from a comparison of FIGS. 7 and 11, the tubing product 12 may be bent sharply (i.e., bent to a small radius even so sharply that adjacent ones of the support beads 34 touch) and both the central passage 29a and the lumen 36 remain open.

Figure 8:
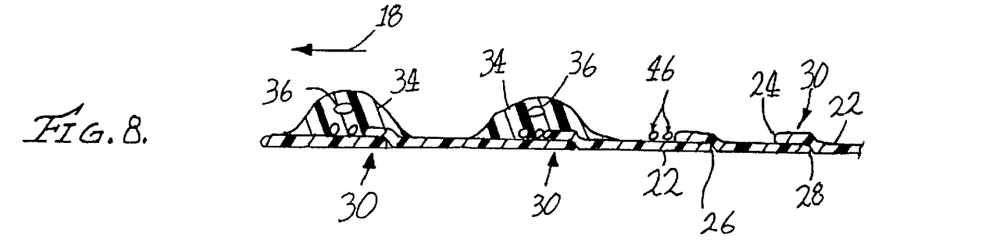
FIG. 8 is a schematic illustration of a work piece cross-section during the manufacturing process, and showing (sequentially) the placement of a molten polymer ribbon which is lap joint bonded, placement of an electrical conductor wire, and placement of an external support-bead feature of the tubing product.

In FIG. 8 it can be further seen that as the ribbon 22 is wrapped about the rolls 14a there occurs a certain amount of overlap of each wrap of the ribbon 22 with the preceding wrap, so as to form successive convolutions, and lap joint 30. Upon the next or a subsequent wrapping or rotation of the formed lap joint, the wire or wires 46 are placed. If more than one wire is placed adjacent to the lap joint 30, then these wires are placed in a parallel position running helically around and along the tubular body 29. Next, upon the same or a subsequent wrapping or rotation of the tubular body 29, the support bead 34 is placed atop the lap joint 30, and over the wires 46. This support bead is preferably setting atop the left-most of the lap joints 30 as seen in FIG. 8, with the tubing product proceeding from right to left in this fragmentary cross sectional view. In this view can be seen the support bead 34 as it appears in cross sectional view. The lumen 36 can be seen, as well as the wires 46, which are partly embedded into the ribbon 22 and encapsulated by the support bead 34. FIG. 9 provides an enlarged view of this cross section of the tubing product 12, and it can be noted that the wires 46 each have an individual insulation or insulation jacket (indicated by arrow 98) about the two or more of them. This individual or jacket form of insulation 98 surrounds the one, two, or plural wires 46 to insulate and separate them from one another. In the instance of insulation for wires 46 being formed as a jacket 98 surrounding two or more of the wires 46, this jacket may be formed of a selected material that is the same as or different than the ribbon 22 and bead 34. For example, the jacket 98 may be constructed of polyurethane. This jacket surrounds the conductors 46, and spans the spacing between the conductors so that the conductors 46 make up a small twin-lead or multi-conductor ribbon cable construction. The use of electrical conductors 46 in the tubing product 12 is not limiting, however, because the tubing product 12 may be made with only a single wire 46 or with no wire at all.

Figure 10:
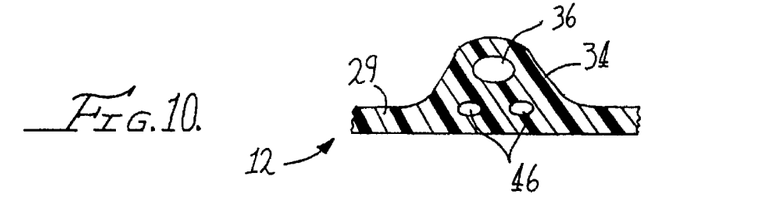
FIG. 10 is an enlarged cross section view of a wall portion of the tubing product of FIG. 9 illustrating the resulting unitary construction for the tubing wall, helical support bead, helical lumen, and electrical conductor wire of the tubing product.

Also depicted in both FIGS. 9 and 10 is a cross sectional view of the lumen 36 present inside the support bead 34. The support bead 34 is constructed as described above so that the lumen 36 retains a substantially uniform shape and size throughout its helical length, from one end to the other end of a length of the tubing product. As can also be seen particularly in FIG. 10 the separation distance between the wire or wires 46 and the internal passage 29a of the tubing product 12 is much less than that between the resistance wire 46 and either of the lumen 36 or the ambient outside of the tubing product 12. Therefore, heat loss to the ambient from the wire 46 when this wire serves as an electrical resistance heating element will be minimal. On the other hand, heat transfer from this wire 46 to, for example, tidal air flow in the passage 29a, will be excellent. That is, electrical heating of conductors 46 (i.e., by passing an electrical current through them), will also effectively heat a tidal air flow in the central passage 29a, as well as in lumen 36. Simultaneously, support bead 34 and lumen 36 will act as insulators between the conductors and ambient.

Figure 12:
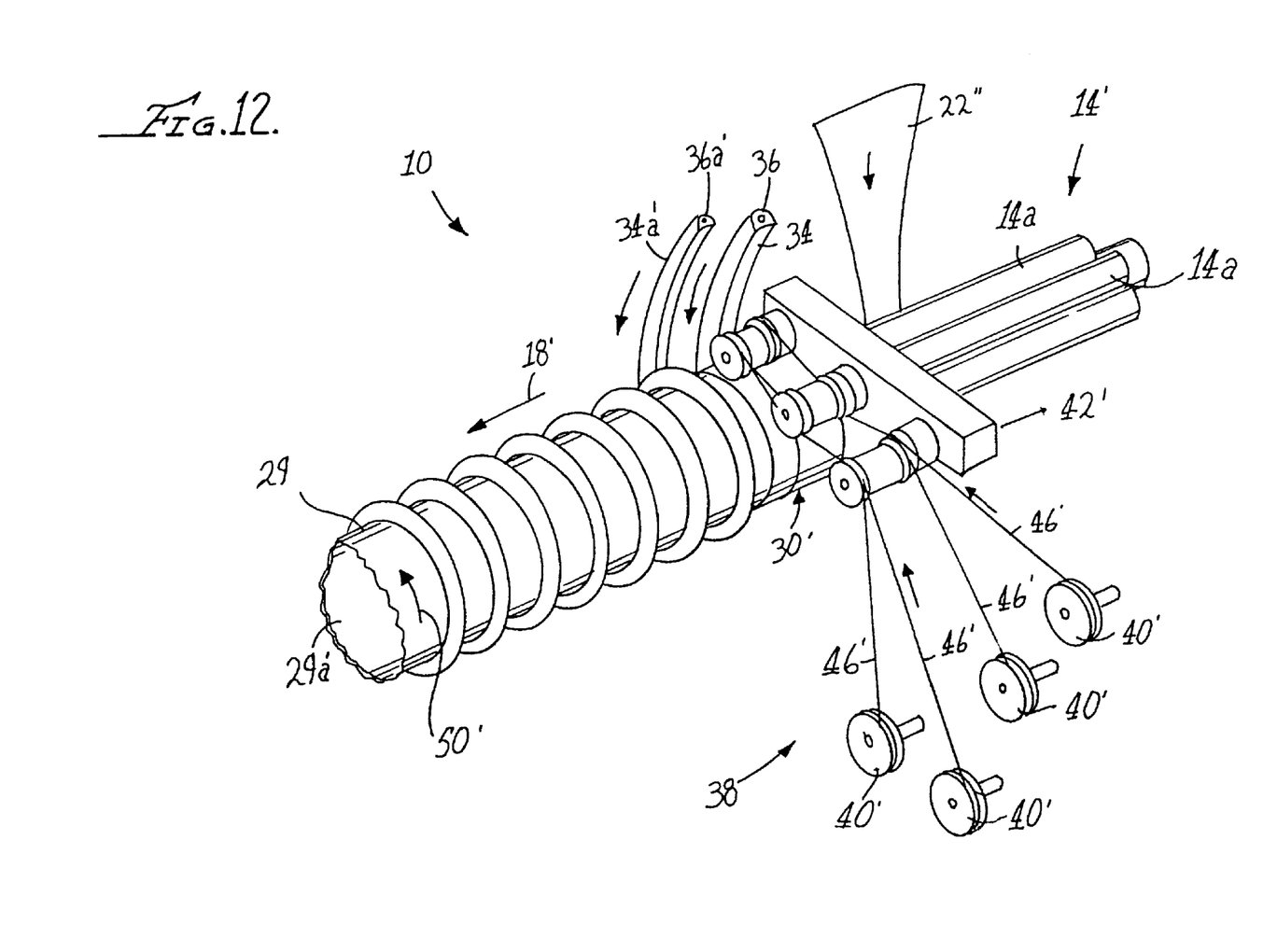
FIG. 12 is a diagrammatic perspective view showing an alternative arrangement of a manufacturing apparatus and an alternative embodiment of a tubing product made using this apparatus according to the present invention.
Figure 13:
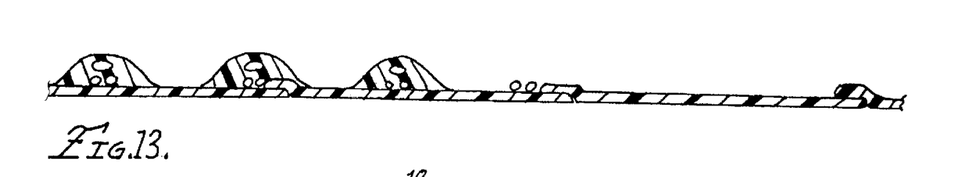
FIG. 13 is a schematic illustration of a work piece in fragmentary cross-section showing the sequential placement of: a ribbon extrudate, an electrical conductor wire, and two interdigitated external support-bead features according to the alternate embodiment of the invention seen in FIG. 12.
Figure 14:
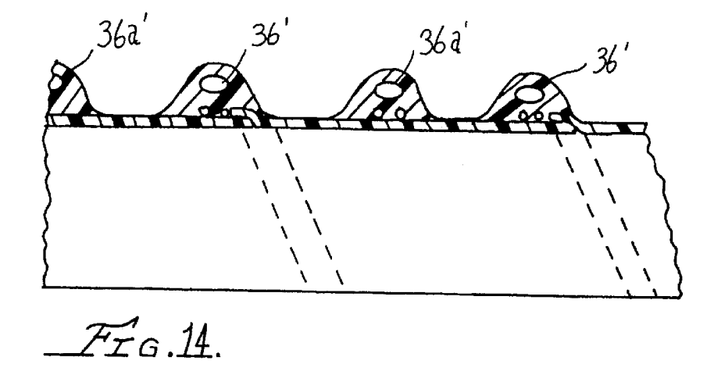
FIG. 14 provides an enlarged fragmentary cross-sectional view showing the alternate embodiment of the invention resulting from the process illustrated by FIGS. 12 and 13.

In FIGS. 12, 13, and 14 an alternative embodiment of the invention is presented. In order to obtain reference numerals for use in describing the embodiment of these Figures, features which are the same, or which are analogous in structure or function to those described above, are referenced with the same numeral used above, and having a prime added thereto.

FIG. 12 illustrates an apparatus 10' including a mandrel 14' having four cantilevered and rotationally driven winding rolls 14a'. According to this alternative embodiment, dual support beads 34' and 34a' are wrapped onto the tubular body 29' formed by the wrapped and self-bonded ribbon 22'. Each of the support beads encapsulate one or a pair of wires 46' with the second support bead 34a' being positioned axially between wraps of the support bead 34' (and between the lap joints 30'), and adhering to the ribbon 22' in a centralized location. In each of the support beads 34' and 34a', a lumen 36' and 36a' can be seen in FIG. 14, particularly. It can further be seen that apparatus 10' includes wire feeding mechanism 38' for feeding and embedding plural electrically conductive wires 46' from wire spools 40'.

Again, as the ribbon 26' is fed onto the winding rolls 14a', as can be seen in FIG. 12, the tubular body 29' advances axially forward (arrow 18'). The wire 46' (or plural such wires, as explained above) is laid next to the lap joint 30', and is then covered over by the support bead 34'. Intermediate of the lap joints 30', an additional wire 46' (or plural such wires) is laid atop the ribbon 22', and is covered over and encapsulated by the second support bead 34a'. Each of the support beads 34' and 34a' may define a respective lumen 36' and 36a'. Again, the lumens 36' and 36a' are maintained open, and their size is controlled to a substantially uniform dimension by application of a controlled internal air pressure. As those ordinarily skilled in the pertinent arts will appreciate, the beads 34' and 34a' may be produced by separate extruders and separated cross heads (recalling FIG. 4, and the description of this Figure above), or these beads may be produced by a single extruder having a single cross head with a die having a pair of shaped openings each for producing one of the beads 34' and 34a'.

Figure 15:
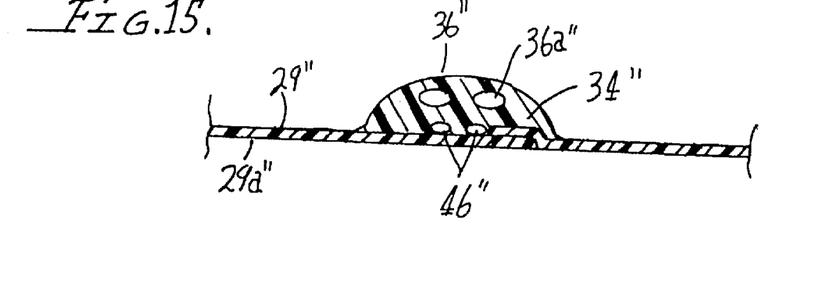
FIG. 15 provides a schematic view of yet another embodiment of a tubing product according to this invention, and having plural parallel helical lumens in a single helical support bead.

In FIG. 15 yet another alternative embodiment of the invention is presented. In order to obtain reference numerals for use in describing this embodiment, features which are the same, or which are analogous in structure or function to those described above, are referenced with the same numeral used above, and having a double prime added thereto.

FIG. 15, provides a cross sectional view of a tubing product 12" with a tubular body 29" (i.e., similar to a portion of FIGS. 8 and 13, or similar to FIGS. 9, 10, or 14) depicting a bead 34" atop a pair of conductors 46", and defining plural lumens 36" and 38a". These plural lumen 36" and 36a" each have a stable, uniform shape and size throughout the helical length of the bead 34" from one end to the other end of a length of the tubing product 12. Because the support bead 34" defines in this embodiment a pair of lumens, the lumens 36" and 36a" may each be used, for example, to conduct a separate fluidic or fluid pressure signal from one end to the other end of a length of the tubing product 12".

Figure 16:
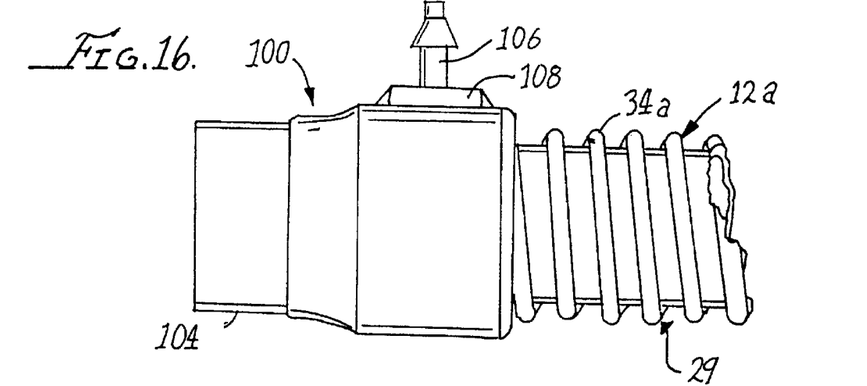
FIG. 16 is a side elevation view of a length of the tubing product having an integrally molded end fitting which terminates both the central passage of the tubing product and the lumen of the support bead.
Figure 17:
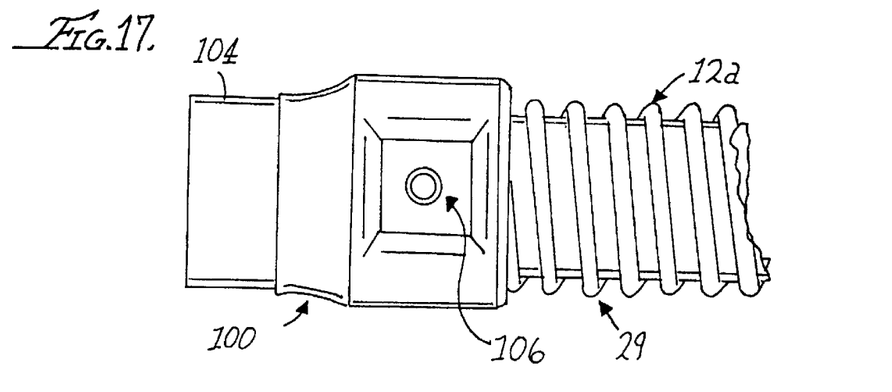
FIG. 17 is a plan view of the length of tubing product seen in FIG. 16.
Figure 18:
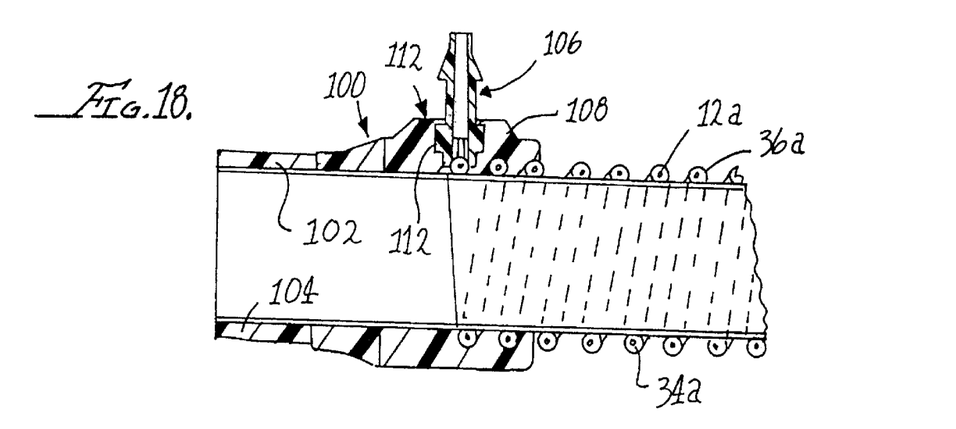
FIGS. 18 and 19 are respective cross sectional views taken at lines 18—18, and 19—19, of FIGS. 16 and 17, respectively.
Figure 19:
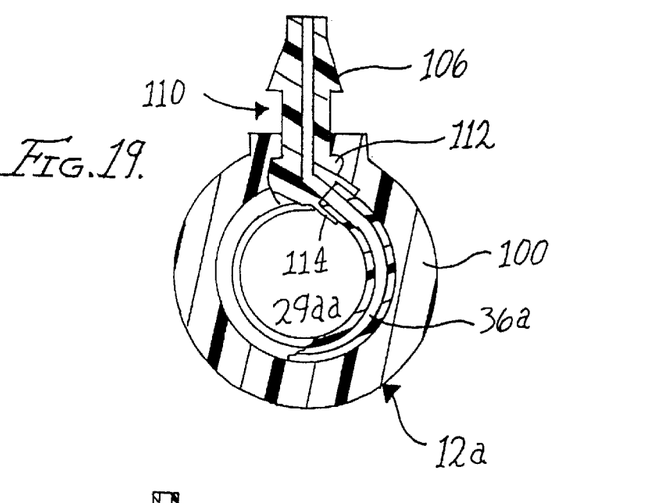

Turning now to FIGS. 16 through 19 in conjunction with one another, an embodiment of the tubing product having an integrally formed end termination fitting or end connection feature is illustrated. This end termination fitting (hereinafter, "end fitting") provides for connection of both the central passage of the tubing 12a, and of the lumen 36a, in fluid flow relation with respective sources or receivers of fluid flow. In order to obtain reference numerals for use in describing this alternative embodiment, features which are the same as or analogous in structure or function to those depicted and described above are referenced with the same numeral used above, and having an "a" added. The length of tubing product 12a includes a tubular body 29a with an internal passage 29aa. In this embodiment, however, the support bead 34a is almost circular in cross sectional shape, as is best seen in FIG. 18. This support bead defines a lumen 36a, as will be familiar to the reader by this point in the disclosure. Integrally attached at an end portion of the tubing 12a is an end termination or end fitting 100. This end fitting is preferably formed integrally on and bonding to the end portion of the tubing 12a. As those ordinarily skilled in the pertinent arts will appreciate, and as will be further explained below, the integral forming of the end fitting 100 on the tubing 12a is preferably accomplished by the use of injection molding. Thus, it is to be appreciated that the fitting 100 is formed of a resilient shape-retaining, but yieldable polymer material. As is best seen in FIGS. 18 and 19 the end fitting 100 defines a through passage 102 which communicates outwardly from the central passage 29aa of the tubing 12a. Outwardly of the opening of this passage 102, the fitting 100 defines a tapering outer surface portion 104, which may be received, for example, snugly and in fluid-tight relation into a slightly tapering fitting bore of another fitting or machine (not shown) to which the tubing 12a is to be connected in fluid flow relation. In order to also provide for connection of the lumen 36a in such a fluid flow relation, the fitting 100 also carries an outwardly extending hose barb feature 106 which is in fluid flow communication with the lumen 36a. The hose barb feature 106 extends outwardly from a slightly raised boss 108 defined on the outer surface of the end fitting 100.

FIGS. 18 and 19 best illustrate that the hose barb feature 106 is an integral part of a lumen termination fitting 110 integrally imbedded into and forming a part of the end fitting 100. The lumen termination fitting 110 includes a body portion 112 disposed immediately adjacent to the tubular body 29a of the tubing product 12a, and from which the hose barb feature extends radially outwardly through the material of the end fitting 100 to extend outwardly of this end fitting. The lumen termination fitting 110 also includes an angularly disposed collar portion 114 extending tangentially of the tubing product 12a within the end fitting 100, and integrally bonding to a short section of the bead 34a, so that the lumen 36 communicates with this lumen termination fitting.

Figure 20:
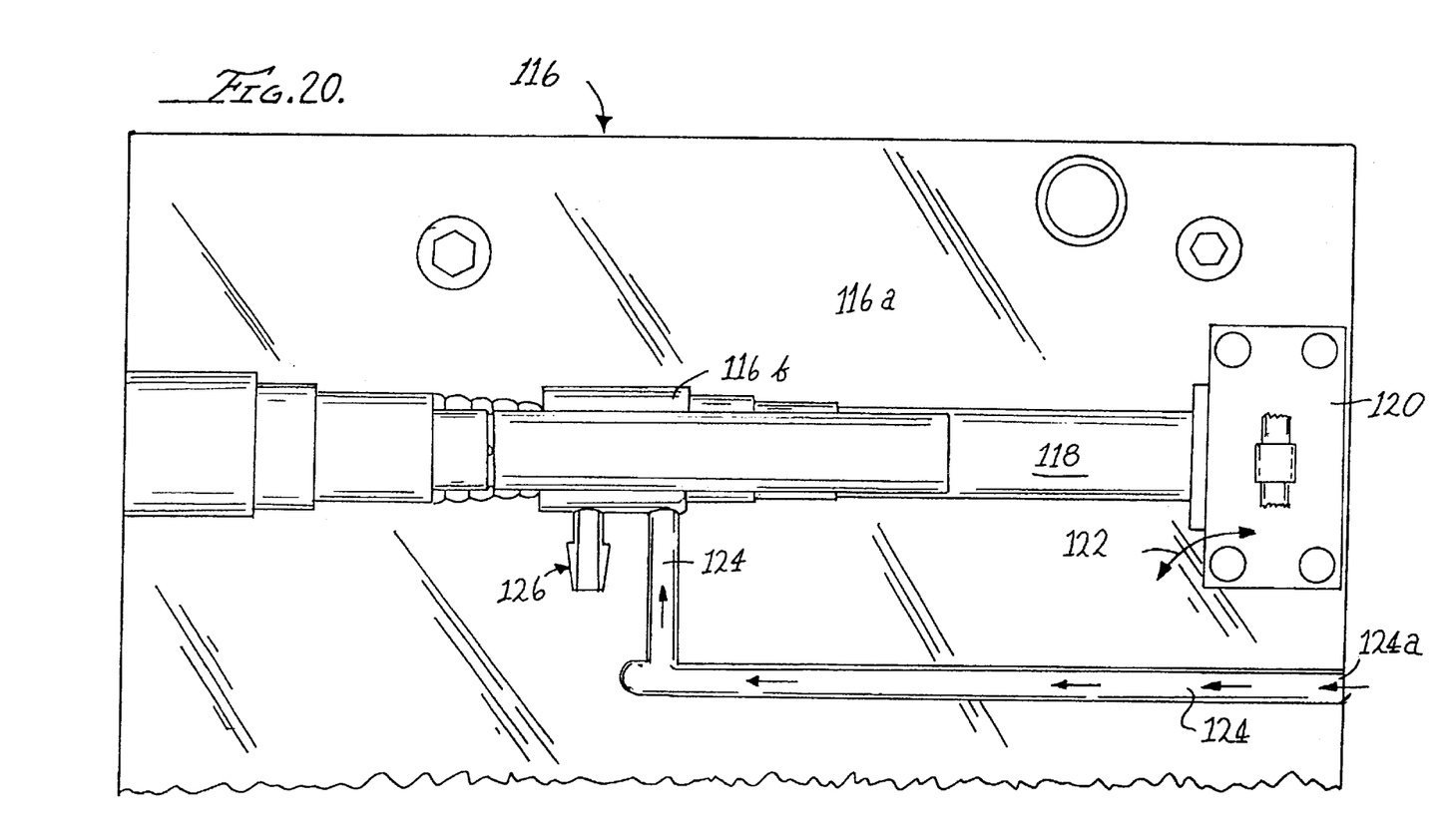
FIG. 20 provides a fragmentary plan view of an injection molding die used in a method of manufacturing the tubing product with integral end fitting as seen in FIGS. 16–19.

Considering now FIG. 20, the lower part 116a of an injection molding die apparatus 116 is illustrated. This die apparatus 116 is utilized in an injection molding process to form the end fitting 100 on a length of the tubing product 12a, and to simultaneously bond the lumen termination fitting 110 to a short outwardly tangentially extending end portion of the support bead 34a. The portion of apparatus which is not shown in FIG. 20 will be understood by those ordinarily skilled in the injection molding arts to be an upper portion of the die, which upper portion is essentially a mirror image of the lower part 116a shown in FIG. 20 (with the exception of features to be noted). FIG. 20 shows the lower portion 116a of the injection molding die 116, which lower portion 116a defines one-half 116b of the die cavity (the other half being defined in the upper half of the die—not seen in FIG. 20), and includes a pivotal core pin 118. The core pin 118 is carried on the lower half 116a of the die 116, and a core pin 118 is not found on the upper portion of the die (again, the upper mirror-image portion of the die 116 not being seen in FIG. 20). The pivotal core pin 118 is pivotal on a hinge mechanism 120 carried on the lower die part 116a. The core pin 118 is pivotal between a first position in the cavity 116b (as seen in FIG. 20) preparatory to an injection molding operation, and a second position in which the left hand end (as seen in FIG. 20) of the core pin is pivoted up out of the die cavity (as is indicated by arrow 122 on FIG. 20) both to allow a length of tubing product to be inserted partially over this die pin before the injection molding step, or to allow the length of tubing product and its integrally molded end fitting to be removed from the core pin and cavity 116b following the injection molding step. A sprue passage 124 (half formed in each half of the die 116) extends from an injection port 124a to the cavity 116b. At the injection port 124a, those ordinarily skilled will understand that the die 116 receives molten polymer material from the injection nozzle (not shown) an injection molding ram (also not shown).

As is seen in FIG. 20, the cavity 116b also includes a recess 126 for receiving and holding a lumen termination fitting 110 in preparation for the injection molding step. This recess 126 embraces the hose barb portion 106 of the lumen termination fitting 110, which is also slipped on and supported on an end of the bead 34a within cavity 116b in preparation for closing of the die 116. After the die 116 is closed (i.e., by bringing together the die portion 116a and its matching upper mirror-image portion), then molten polymer is injected via the sprue passage 124. The molten polymer material both forms the end fitting 110 and simultaneously provides sufficient heat and pressure to integrally bond the bead 34a within the collar portion 114 of the lumen termination fitting 110. Thus, the lumen 36a is sealingly connected in fluid flow relation to the hose barb 106. When the molten polymer has hardened, the die 116 is opened and the fitting as seen in FIGS. 16 and 17 is drawn off the core pin 118 along with the attached length of tubing product 12a.

Figure 21:
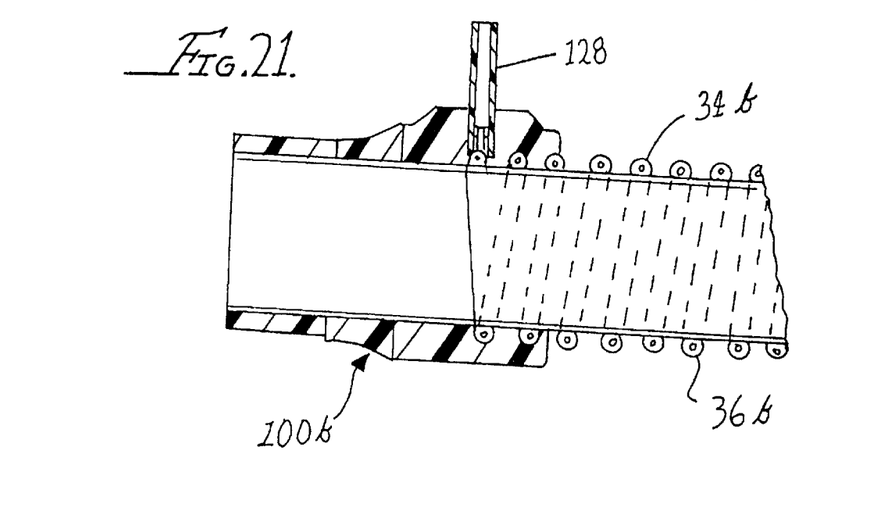
FIGS. 21 and 22 are respective longitudinal and cross sectional views similar to FIGS. 18 and 19, but illustrating an alternative embodiment of the tubing product with integral end fitting.
Figure 22:
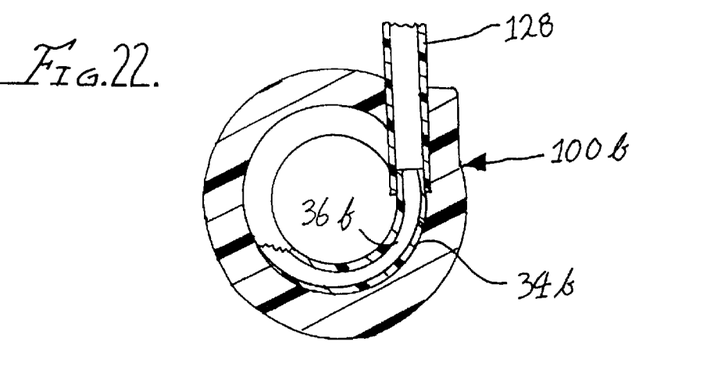

FIGS. 21 and 22 illustrate an alternative embodiment of the present invention, in which an end fitting 100b is provided with an outwardly extending "pig tail" of small sized tubing 128. The "pig tail" of small tubing 128 emerges from a boss 108b formed on the end fitting 100b, and is integrally bonded both to this end fitting 100b, and to an end portion of the support bead 34b, as is seen in the drawing Figures. In view of the description and explanation above of the apparatus and method presented by FIGS. 16–20, those ordinarily skilled in the pertinent arts will understand that the apparatus of FIGS. 21 and 22 is made using a similar injection molding method, but with a die cavity simply providing for the tubing 128 to be received on the end of the support bead 34b, and to be bonded to this support bead simultaneously with the injection molding step forming the end fitting 100b.

Those skilled in the art will further appreciate that the present invention may be embodied in other specific forms without departing from the spirit or central attributes of the invention. Because the foregoing description of the present invention discloses only particularly preferred exemplary embodiments of the invention, it is to be understood that other variations are recognized as being within the scope of the present invention. Accordingly, the present invention is not limited to the particular embodiments which have been described in detail herein. Rather, reference should be made to the appended claims which define the scope and content of the present invention.

I claim:

1. A thin-walled, flexible and collapse-resistant plastic tubing having a substantially smooth bore and a helical outer support bead, said tubing comprising:

a flexible tubing wall formed of elongate thermoplastic ribbon having opposite side edges, said ribbon being helically wrapped on itself to overlap said opposite side edges a certain amount forming a helical lap joint whereat opposite side edge portions of said ribbon are heat-bonded to one another so that a thin-walled elongate tubular body is formed;

a helical support bead upon and heat bonded to said flexible tubular body atop of said helical lap joint, said support bead integrally bounding a helical lumen; and a helical electrical conductor embedded in said tubing atop of said tubular body adjacent to said lap joint and under said helical support bead.

2. The tubing of claim 1 wherein said support bead is free of a helical bonding or sealing line extending between said lumen and ambient, whereby said lumen is free of unintended fluid communication to ambient.

3. The tubing of claim 2 wherein said lumen defines a substantially constant passage size from one end helically to the other end of a length of said tubing.

4. The tubing of claim 1 wherein said support bead defines plural lumens helically extending in parallel within said support bead from one end to the other end of a length of said tubing.

5. The tubing of claim 1 wherein said tubing includes plural electrical conductors in parallel and extending helically in said tubing adjacent to said lap joint.

6. The tubing in claim 1 wherein said electrical conductor is formed of a resistance heating material, whereby said electrical conductor provides a resistance heating conductor insulated from ambient by said support bead and having a comparatively high heat transfer coefficient to the interior of the tubing.

7. The tubing of claim 6 wherein said resistance heating conductor is formed of a nickel chromium alloy.

8. The tubing of claim 1 wherein said elongate plastic ribbon and said elongate support bead are formed of the same material.

9. A thin-walled, flexible and collapse-resistant plastic tubing having a substantially smooth bore and a helical outer support bead, said tubing comprising:

a flexible tubing wall formed of elongate thermoplastic ribbon having opposite side edges, said ribbon being helically wrapped on itself to overlap said opposite side edges a certain amount forming a helical lap joint whereat opposite side edge portions of said ribbon are heat-bonded to one another so that a thin-walled elongate tubular body is formed;

a helical support bead upon and heat bonded to said flexible tubular body atop of said helical lap joint, said support bead integrally bounding a helical lumen;

wherein said lumen has a cross sectional shape perpendicularly to the helix of said lumen, which cross sectional shape is substantially circular, whereby said support bead may be separated from an end of said tubing and said lumen may be connected to a hose barb.

10. The tubing of claim 9 wherein said support bead defines plural lumens each substantially circular in cross sectional shape, and each extending helically in said support bead from one end to another end of a length of the tubing.

11. The tubing in claim 10 wherein said support bead is free from joints or sealing lines extending from any one of said plural lumens to ambient, so that each of said plural lumens is free from communication with ambient between one end and another end of a length of the tubing.

\* \* \* \* \*